(12) United States Patent
Dhanasingh et al.

(10) Patent No.: US 11,426,593 B2
(45) Date of Patent: Aug. 30, 2022

(54) COCHLEAR IMPLANT WITH CLIPPABLE MAGNET

(71) Applicant: MED-EL Elektromedizinische Geraete GmbH, Innsbruck (AT)

(72) Inventors: Anandhan Dhanasingh, Innsbruck (AT); Claude Jolly, Innsbruck (AT); Martin Zimmerling, Patsch (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 130 days.

(21) Appl. No.: 16/084,273

(22) PCT Filed: Mar. 27, 2017

(86) PCT No.: PCT/US2017/024228
§ 371 (c)(1),
(2) Date: Sep. 12, 2018

(87) PCT Pub. No.: WO2017/172566
PCT Pub. Date: May 10, 2017

(65) Prior Publication Data
US 2019/0076661 A1    Mar. 14, 2019

Related U.S. Application Data

(60) Provisional application No. 62/314,430, filed on Mar. 29, 2016.

(51) Int. Cl.
*A61N 1/375* (2006.01)
*A61N 1/05* (2006.01)
(Continued)

(52) U.S. Cl.
CPC .............. *A61N 1/375* (2013.01); *A61N 1/05* (2013.01); *A61N 1/0541* (2013.01);
(Continued)

(58) Field of Classification Search
CPC ...... A61N 1/375; A61N 1/36038; A61N 1/05; A61N 1/0541; A61N 1/372; A61N 1/37252
(Continued)

(56) References Cited

U.S. PATENT DOCUMENTS 8,340,774 B2    12/2012    Hochmair et al.
9,210,521 B2    12/2015    Kasic et al.
(Continued)

OTHER PUBLICATIONS

International Searching Authority/US, International Search Report and the Written Opinion of the International Searching Authority, Application No. PCT/US2017/024228, dated May 25, 2017, 10 pages.
(Continued)

*Primary Examiner* — William J Levicky
(74) *Attorney, Agent, or Firm* — Sunstein LLP

(57) ABSTRACT

An implantable medical device includes an implantable coil case that contains a communications coil. A magnet receptacle is located within the coil case at the radial center and has a magnet opening in one of the lateral surface or the medial surface of the coil case. A magnet fitting groove is recessed into one of the lateral or medial surface of the coil case and extends from the magnet opening to the outer circumference of the coil case. A u-shaped implant magnet clip has parallel clip legs that are connected at a closed end of the u-shape, and an implant magnet is attached to one of the clip legs. The coil case and the magnet clip are configured to cooperate for a portion of the coil case to fit between the clip legs and the implant magnet to slide through the magnet fitting groove and fit through the magnet opening into the magnet receptacle.

15 Claims, 5 Drawing Sheets

(51) Int. Cl.
*A61N 1/36* (2006.01)
*A61N 1/372* (2006.01)

(52) U.S. Cl.
CPC ......... *A61N 1/36038* (2017.08); *A61N 1/372* (2013.01); *A61N 1/37252* (2013.01)

(58) Field of Classification Search
USPC ........................................................ 607/137
See application file for complete search history.

(56) References Cited

U.S. PATENT DOCUMENTS

| | | |
|---|---|---|
| 2008/0009920 A1 | 1/2008 | Gibson et al. |
| 2008/0221641 A1* | 9/2008 | Hochmair ............... A61F 11/04 607/57 |
| 2011/0284014 A1 | 11/2011 | Cadeddu et al. |
| 2015/0087892 A1 | 3/2015 | Tourrel et al. |
| 2015/0359553 A1* | 12/2015 | Harnisch ............ A61N 1/36036 606/210 |

OTHER PUBLICATIONS

IP Australia, Australian Government, Examination Report No. 1, Application No. 2017241456, dated Dec. 8, 2018, 2 pages.

* cited by examiner

COCHLEAR IMPLANT WITH CLIPPABLE MAGNET

This application claims priority from U.S. Provisional Patent Application 62/314,430, filed Mar. 29, 2016, which is incorporated herein by reference in its entirety.

FIELD OF THE INVENTION

The present invention relates to implantable medical devices, and specifically, to removable magnetic elements in such devices.

BACKGROUND ART

Some hearing implants such as Middle Ear Implants (MEI's) and Cochlear Implants (CI's) employ cooperating attachment magnets located in the implant and the external part to magnetically hold the external part in place over the implant. For example, as shown in FIG. 1, a typical cochlear implant system may include an external transmitter housing 101 containing transmitting coils 102 and an external attachment magnet 103. The external attachment magnet 103 has a conventional cylindrical disc-shape and a north-south magnetic dipole having an axis that is perpendicular to the skin of the patient to produce external magnetic field lines 104 as shown. Implanted under the patient's skin is a corresponding receiver assembly 105 having similar receiving coils 106 and an implant magnet 107. The implant magnet 107 also has a cylindrical disc-shape and a north-south magnetic dipole having a magnetic axis that is perpendicular to the skin of the patient to produce internal magnetic field lines 108 as shown. The internal receiver housing 105 is surgically implanted and fixed in place within the patient's body. The external transmitter housing 101 is placed in proper position over the skin covering the internal receiver assembly 105 and held in place by interaction between the internal magnetic field lines 108 and the external magnetic field lines 104. Rf signals from the transmitter coils 102 couple data and/or power to the receiving coil 106 which is in communication with an implanted processor module (not shown).

One problem arises when the patient undergoes Magnetic Resonance Imaging (MRI) examination. Interactions occur between the implant magnet and the applied external magnetic field for the MRI. As shown in FIG. 2, the direction magnetization $\bar{m}$ of the implant magnet 202 is essentially perpendicular to the skin of the patient. In this example, the strong static magnetic field $\bar{B}$ from the MRI creates a torque $\bar{T}$ on the internal magnet 202, which may displace the internal magnet 202 or the whole implant housing 201 out of proper position. Among other things, this may damage the adjacent tissue in the patient. In addition, the external magnetic field $\bar{B}$ from the MRI may reduce or remove the magnetization $\bar{m}$ of the implant magnet 202 so that it may no longer be strong enough to hold the external transmitter housing in proper position. The implant magnet 202 may also cause imaging artifacts in the MRI image, there may be induced voltages in the receiving coil, and hearing artifacts due to the interaction of the external magnetic field $\bar{B}$ of the MRI with the implanted device. Torque and forces acting on the implant magnet and demagnetization of the implant magnet are especially an issue with MRI field strengths exceeding 1.5 Tesla.

Thus, for existing implant systems with magnet arrangements, it is common to either not permit MRI or at most limit use of MRI to lower field strengths. Other existing solutions include use of a surgically removable magnets (e.g. U.S. Pat. No. 8,255,058, incorporated herein by reference in its entirety), spherical implant magnets (e.g. U.S. Pat. No. 7,566,296, incorporated herein by reference in its entirety), and various ring magnet designs (e.g., U.S. Patent Publication 20120238799, incorporated herein by reference in its entirety). U.S. Pat. No. 8,634,909 (incorporated herein by reference in its entirety) describes an implant magnet having a magnetic dipole with a magnetic axis that is parallel to the end surfaces of a disc shaped implant magnet—that is, perpendicular to the conventional magnetic axis of a disc-shaped implant magnet. The magnet is then held in a magnet receptacle that allows the magnet to rotate in response to an external magnetic field such as from an MRI.

Some devices also add a stiffening ring around the magnet to resist torques and help hold the magnet in place. FIG. 3 shows an example of a cochlear implant device 300 with an implantable stimulator 301 that provides electrical stimulation signals to an electrode lead 302 that is implanted in the patient's cochlea. A coil case 303 is made of biocompatible resilient material such as molded silicone in which is embedded a communications coil 304 for transcutaneous communication of an implant communication signal. In the center of coil case 303 is an implant magnet 306 that cooperates with another external holding magnet (not shown) to hold an external coil on the skin of the patient over the implanted communications coil 304. Also embedded in the resilient material of the coil case 303 between the communications coil 304 and the implant magnet 306 is a stiffening ring 305 made of stiffer material than the coil case 303. The stiffening ring 305 is configured to resist mechanical torque movement of the coil case 303 and to promote securement of the implant magnet 306 within the coil case 303. This includes securement of the implant magnet 306 against movement and tilting, and in the case of a removable implant magnet 306, additionally against magnet displacement in lateral direction (i.e. perpendicular to the skin surface).

SUMMARY OF THE INVENTION

Embodiments of the present invention are directed to an implantable medical device that includes an implantable coil case, the coil case having a lateral surface, a medial surface, a radial center, and an outer circumference and containing a communications coil for transcutaneous communication of an implant communication signal. A magnet receptacle is located within the coil case at the radial center and has a magnet opening in one of the lateral surface or the medial surface of the coil case. A magnet fitting groove is recessed into one of the lateral or medial surface of the coil case and extends from the magnet opening to the outer circumference of the coil case. A u-shaped implant magnet clip has parallel clip legs that are connected at a closed end of the u-shape, and an implant magnet is attached to one of the clip legs. The coil case and the magnet clip are configured to cooperate for a portion of the coil case to fit between the clip legs and the implant magnet to slide through the magnet fitting groove and fit through the magnet opening into the magnet receptacle.

In further specific embodiments, the magnet receptacle has an angled side wall adjacent to the magnet fitting groove. The implant magnet clip may also include a clip handling projection configured for surgical grasping to manipulate the implant magnet clip. The coil case may be made of silicone material. The magnet clip may be made of biocompatible polymer material such as PEEK, PTFE or FEP. The implant magnet may have a magnetic field direction within the implant magnet that is parallel to the lateral surface. The implant magnet may be rotatably attached to one of clip legs.

In any of the above, the implantable medical device may be a hearing implant system such as a cochlear implant system, a middle ear implant system, or a vestibular implant system, or the implantable medical device may be a laryngeal pacemaker implant system.

DETAILED DESCRIPTION OF SPECIFIC EMBODIMENTS

In existing implantable medical devices such as hearing implants which use implant magnets, even though considerable progress has been made, compatibility with MRI systems remains challenging. For example, removable implant magnets require a relatively large surgical incision over the implant position in order to remove the magnet, and the silicone pouch that holds the magnet loses its shape after just a couple of magnet removals. Embodiments of the present avoid these problems by using a magnet clip that slides over the surface of the implant coil case.

Figure 1:
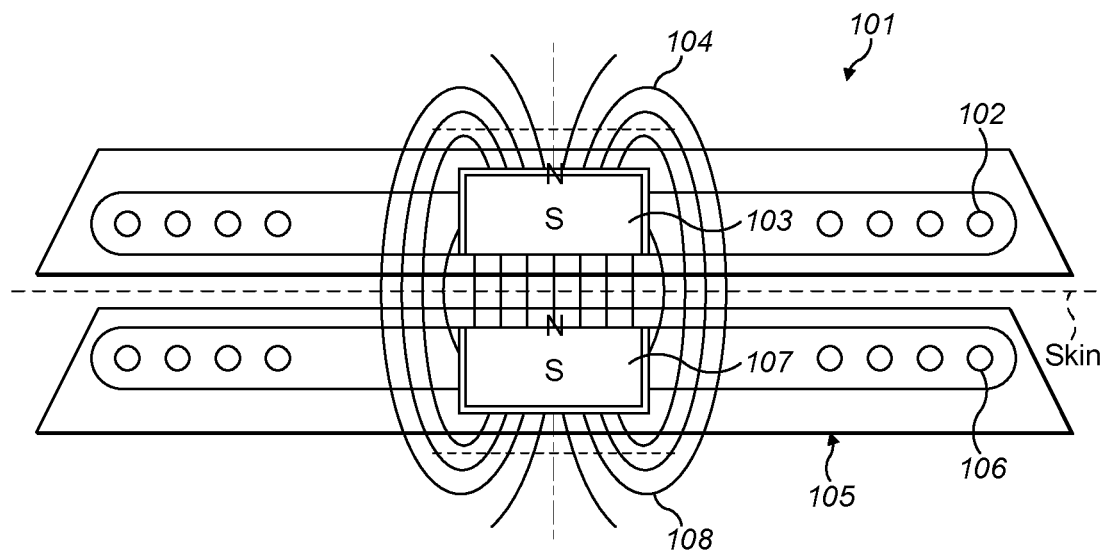
FIG. 1 shows portions of a typical cochlear implant system and the magnetic interaction between the implant magnet and the external holding magnet.
Figure 2:
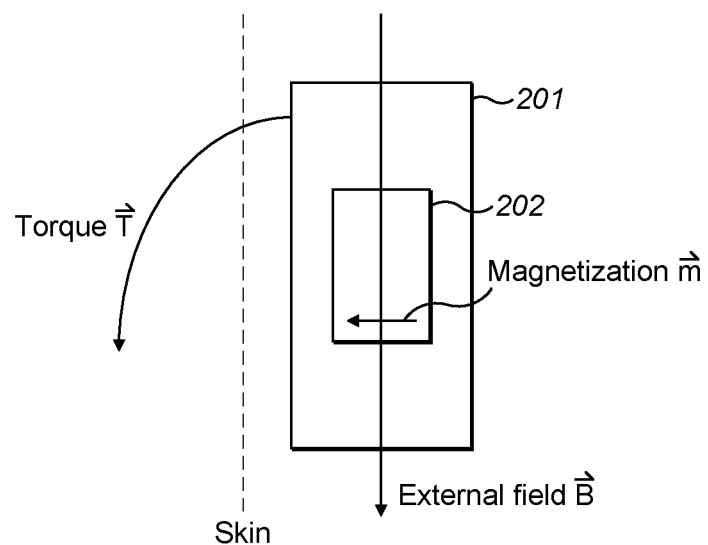
FIG. 2 illustrates the force interactions that can occur between an implant magnet and the applied external magnetic field for an MRI system.
Figure 3:
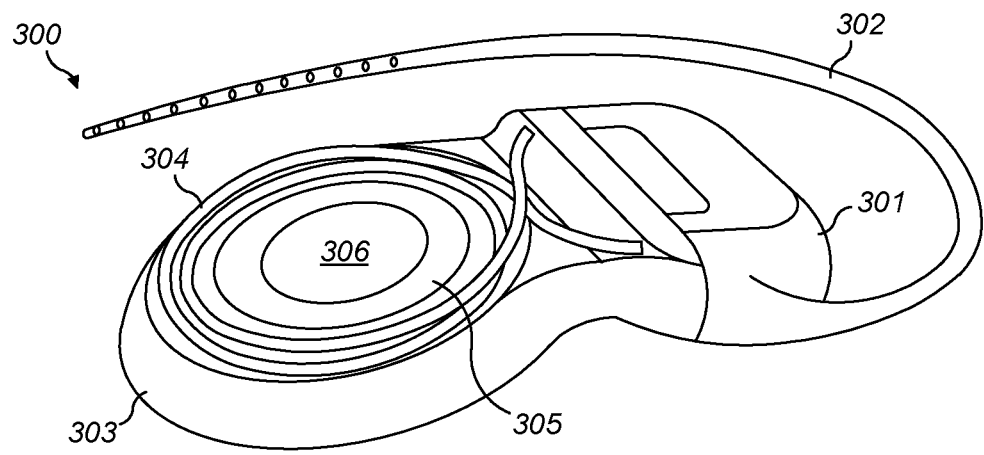
FIG. 3 shows an example of a cochlear implant device with a stiffening ring embedded in the coil case.
Figure 4A:
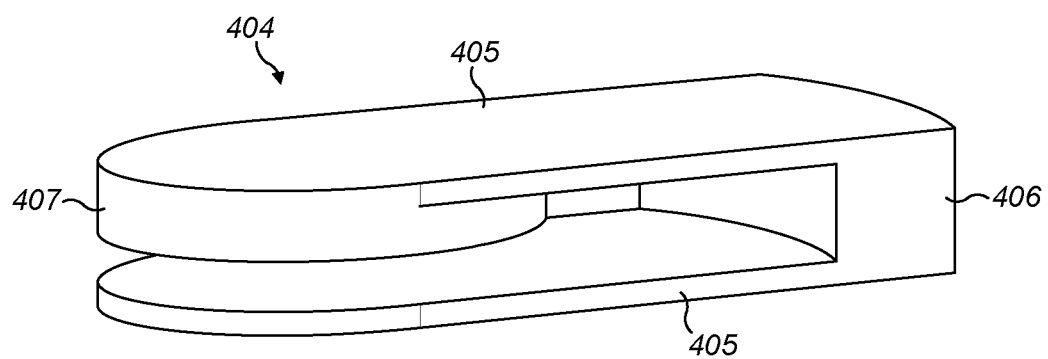
FIG. 4 A-C shows an implantable medical device arrangement according to one embodiment of the present invention.
Figure 4B:
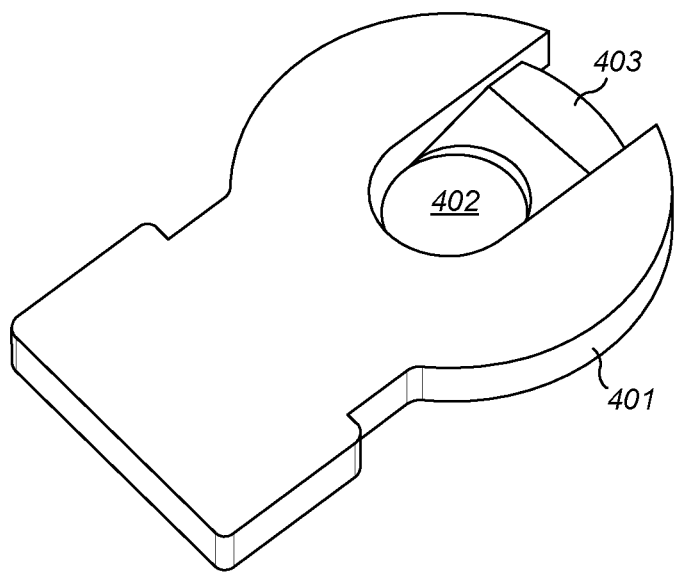

FIG. 4 A-C shows an implantable medical device arrangement according to one embodiment of the present invention. An implantable coil case 401 is typically made of biocompatible silicone material and contains a communications coil for transcutaneous communication of an implant communication signal. A magnet receptacle 402 is located within the coil case 401 at the radial center and has a magnet opening in the lateral surface of the coil case 401. A magnet fitting groove 403 is recessed into the lateral surface of the coil case 401 and extends from the magnet opening to the outer circumference of the coil case 401. In some specific embodiments, the lateral surface of the coil case 401 may be slightly recessed from the outer circumference towards the center magnet opening.

A u-shaped implant magnet clip 404 has parallel clip legs 405 that are connected at a closed end 406 of the u-shape. One of the clips legs 405 has an implant magnet 407 attached to it. In some specific embodiments, the implant magnet 407 may be rotatably attached to one of clip legs 405. The coil case 401 and the magnet clip 404 are configured to cooperate for a portion of the coil case 401 to fit between the clip legs 405 and the implant magnet 407 to slide through the magnet fitting groove 403 and fit through the magnet opening into the magnet receptacle 402. Thus, there is some flexibility and spring at the closed end 406 of the magnet clip 404 so that the opposing legs 405 may spread apart to fit over the coil case 401.

Figure 4C:
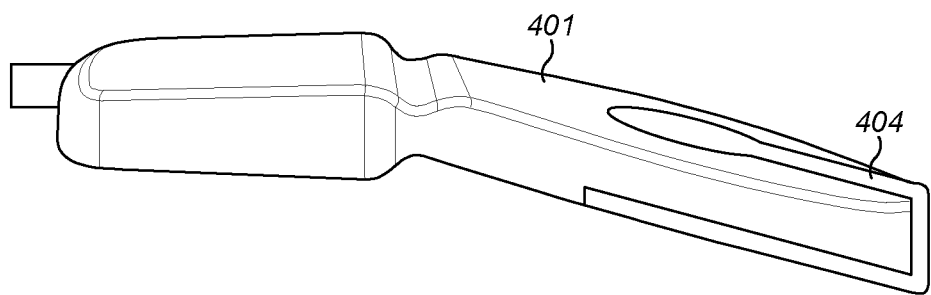

In some specific embodiments, the implant magnet 407 may have a magnetic field direction within the implant magnet that is parallel to the lateral surface of the coil case 401 as described in U.S. Pat. No. 8,634,909. The coil case 401 also may be slightly recessed at the outer circumference and on the bottom medial side so that the outer surface of the magnet clip 404 lies flush against the outer surface of the coil case 401 as shown in FIG. 4C. The magnet clip 404 may be made of biocompatible polymer material such as PEEK, PTFE or FEP. In some embodiments the magnet clip 404 may be made of ferromagnetic material, in which case the implant magnet 407 will magnetically attract the lower leg 405 to increase the fixation of the implant magnet 407 within the magnet receptacle 402. If the magnet clip 404 is made of ferromagnetic material, it may be desirable to cover it with an outer film of biocompatible material such as Parylene. The magnet clip 404 should not be much wider than the diameter of the implant magnet 407 so as to enable use of a small incision when removing the magnet.

Figure 5:
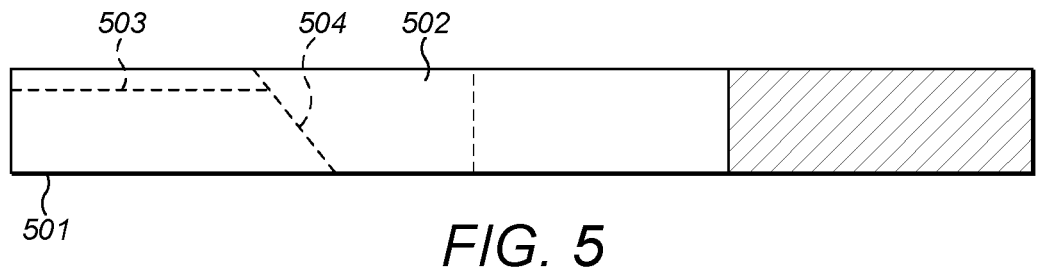
FIG. 5 shows a cross-sectional view of an implantable coil case according to another specific embodiment of the present invention.

FIG. 5 shows a cross-sectional view of an implantable coil case 501 according to another specific embodiment of the present invention where the magnet receptacle 502 has an angled side wall 504 adjacent to the magnet fitting groove 503. The angled side wall 504 improves the ability of the implant magnet to easily slide in and out of the magnet receptacle 502 for removal and replacement procedures.

Figure 6:
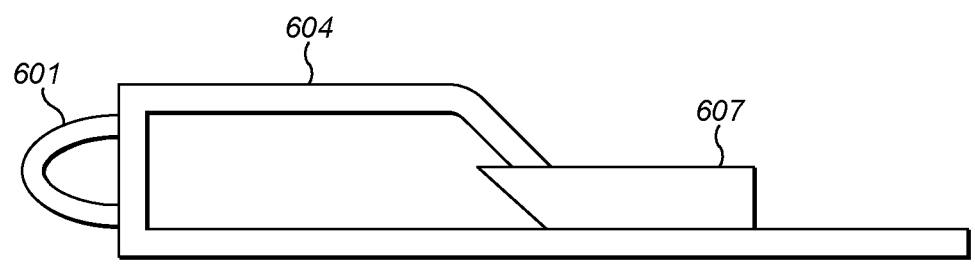
FIG. 6 shows a cross-sectional view of an implant magnet clip according to another specific embodiment of the present invention.

FIG. 6 shows a cross-sectional view of an implant magnet clip 604 and implant magnet 607 according to another specific embodiment of the present invention with a clip handling projection 601 that is configured for surgical grasping to manipulate the implant magnet clip 604. For example, the handling projection 601 may be a loop or eyelet structure that protrudes from the closed end of the magnet clip 604.

Figure 7A:
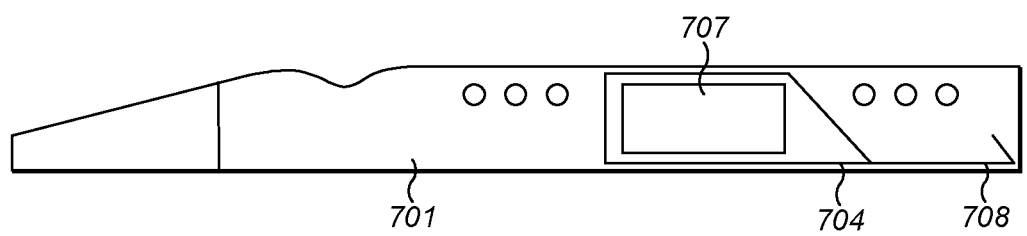
FIGS. 7A-7B show cross-sectional views of an implant magnet clip according to another specific embodiment of the present invention.
Figure 7B:
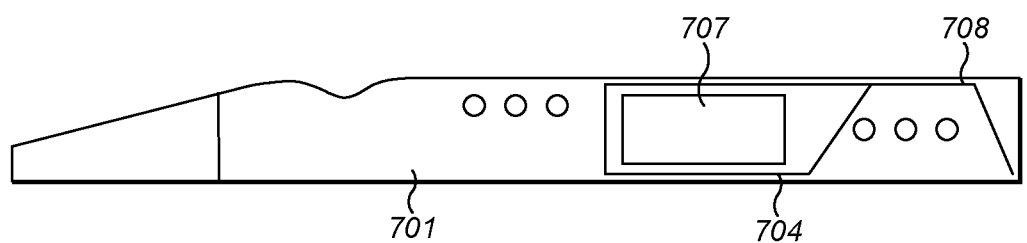

FIG. 7A shows a cross-sectional view of an implant magnet clip 704 according to another specific embodiment of the present invention, which has a bendable leg 708 that fits against the medial side (the bone side) of the coil case 701 with its outer end inwardly bent back over the outer perimeter of the coil case 701 parallel to the implant magnet 707 so as to secure the magnet clip 704 in place. The implant magnet 707 enters the coil case 701 through the medial side. In this embodiment, the magnet clip 704 does not have a portion that fits on the lateral side of the coil case 701 (the skin side), which may be better in terms of coupling of the implant communications signal across the skin into the receiver coil within the coil case without being affected by the magnet clip 704. FIG. 7B shows a cross-sectional view of a slightly different embodiment of a magnet clip 704 where the bendable leg 708 does pass over the lateral side of the coil case 701, with the bent end forming a trapezoidal shape with the implant magnet 707.

A clippable implant magnet as described above is better suited than prior existing implant magnet arrangements to allow for easy removal of the implant magnet prior to undergoing an MRI simply by means of a minor surgical procedure using a small incision in the skin over the closed end of the magnet clip. The same small incision can then be used after the MRI to replace the magnet clip.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable medical device comprising:
   an implantable coil case containing a communications coil for transcutaneous communication of an implant communication signal, the coil case having a lateral surface, a medial surface, a radial center, and an outer surface located at an outer circumference of the implantable medical device;
   a magnet receptacle within the coil case at the radial center and having a magnet opening in one of the lateral or medial surface;
   a magnet fitting groove recessed into one of the lateral surface or the medial surface of the coil case and extending from the magnet opening at the radial center to the outer circumference at the outer surface of the coil case; and
   an implant magnet clip having a u-shape and comprising:
      i. parallel clip legs connected at a closed end of the u-shape, and
      ii. an implant magnet attached to one of the clip legs;
   wherein the coil case and the magnet clip are configured to allow a portion of the coil case to fit between the clip legs and to allow the implant magnet to slide through the magnet fitting groove and fit into the magnet receptacle.

2. The implantable medical device according to claim 1, wherein the magnet receptacle has an angled side wall adjacent to the magnet fitting groove.

3. The implantable medical device according to claim 1, wherein the implant magnet clip includes a clip handling projection configured for surgical grasping to manipulate the implant magnet clip.

4. The implantable medical device according to claim 1, wherein the coil case is made of silicone material.

5. The implantable medical device according to claim 1, wherein the magnet clip is made of ferromagnetic material.

6. The implantable medical device according to claim 1, wherein the magnet clip is made of polymer material.

7. The implantable medical device according to claim 1, wherein the implant magnet has a magnetic dipole moment configured to be substantially parallel to the top lateral surface.

8. The implantable medical device according to claim 1, wherein the implant magnet is rotatably attached to one of clip legs.

9. The implantable medical device according to claim 1, wherein the implantable medical device is a hearing implant device.

10. The implantable medical device according to claim 1, wherein the implantable medical device is a cochlear implant system, a middle ear implant system, or a vestibular implant system.

11. The implantable medical device according to claim 1, wherein the implantable medical device is a laryngeal pacemaker implant system.

12. The implantable medical device according to claim 1, wherein an outer surface of each of the parallel clip legs are configured to lie flush with the medial surface and the lateral surface respectively.

13. The implantable medical device according to claim 12, wherein an outer surface of the closed end is configured to lie flush with the outer surface of the coil case.

14. The implantable medical device according to claim 1, wherein the implant magnet is configured to be located between the lateral surface and the medial surface of the coil case.

15. The implantable medical device according to claim 1, wherein the implant magnet is a cylindrical disc shaped magnet.

* * * * *